United States Patent
Daeffler et al.

(10) Patent No.: US 8,450,289 B2
(45) Date of Patent: May 28, 2013

(54) COMPOSITIONS COMPRISING A PARVOVIRUS VP1-VARIANT AND A PARVOVIRUS NS1 PROTEIN FOR INDUCTION OF CYTOLYSIS

(75) Inventors: Laurent Daeffler, Dossenheim (DE); Jurg Nuesch, Muttenz (CH); Jean Rommelaere, Heidelberg (DE)

(73) Assignee: Deutsches Krebsforschungszentrum Stiftung des Offenlichen Rechts, Heidelberg (DE)

( * ) Notice: Subject to any disclaimer, the term of this patent is extended or adjusted under 35 U.S.C. 154(b) by 0 days.

(21) Appl. No.: 12/570,913

(22) Filed: Sep. 30, 2009

(65) Prior Publication Data
US 2010/0029751 A1  Feb. 4, 2010

Related U.S. Application Data

(62) Division of application No. 10/483,234, filed as application No. PCT/EP02/07706 on Jul. 10, 2002, now abandoned.

(30) Foreign Application Priority Data

Jul. 10, 2001  (EP) .................................... 01116856

(51) Int. Cl.
*A61K 48/00* (2006.01)
*C12N 15/62* (2006.01)
*C12N 15/35* (2006.01)
*C12N 15/864* (2006.01)
*C12N 5/10* (2006.01)

(52) U.S. Cl.
USPC ................... 514/44 R; 435/320.1; 435/235.1; 435/325; 536/23.4; 536/23.72

(58) Field of Classification Search
None
See application file for complete search history.

(56) References Cited

U.S. PATENT DOCUMENTS 6,458,362 B1  10/2002  Casal et al.
2004/0208886 A1  10/2004  Daeffler et al.

FOREIGN PATENT DOCUMENTS

WO  0030668 A2  6/2000

OTHER PUBLICATIONS

ICTBdB Index of Viruses. 2002. Family 00.050. Parvoviridae. [retrieved on Feb. 8, 2011] Retrieved from the internet :<URL: http://www.ictvdb.org/Ictv/fs_parvo.htm>.*
Kestler et al (Human Gene Therapy 10:1619-1632, 1999).*
Dupont et al (Gene Therapy 7:790-796, 2000; in IDS).*
Welsh et al (Current Opinion in Biotechnology 8:617-622, 1997).*
Corbau et al, Virology 278:151-161, 2000.*
Aasted, Bent, et al., "Vaccination with Aleutian mink disease parvovirus (AMDV) capsid proteins enhances disease, while vaccination with . . . ", "Vaccine", Jul. 1998, pp. 1158-1165, vol. 16, No. 11/12.
Caillet-Fauqet, P., et al., "Programmed killing of human cells by means of an inducible clone of parvoviral genes encoding non-structural proteins", "EMBO J.", Sep. 1990, pp. 2989-2995, vol. 9, No. 9.
Cotmore, S. et al. , "The NS2 Polypeptide of Parvovirus MVM is Required fo rCapsid Assembly in Murine Cells ", "Virology", 1997, pp. 267-280, vol. 231.
Dupont, F., et al., "Tumor-selective gene transduction and cell killing with an oncotropic autonomous parvovirus-based vector", "Gene Therapy", May 2000, pp. 790-796, vol. 7, No. 9.
Gigler, A. et al., "Generation of Neutralizing Human Monoclonal Antibodies against Parvovirus B19 Proteins", "Journal of Virology", Mar. 1999, pp. 1974-1979, vol. 73, No. 3.
Grifman, Mirta, et al., "Incorporation of tumor-targeting peptides into recombinant adeno-associated virus capsids", "Molecular Therapy", Jun. 2001, pp. 964-975, vol. 3, No. 6.
Kestler, Jurgen, et al., "cis Requirements for the Efficient Production of Recombinant DNA Vectors Based on Autonomous Parvoviruses", "Human Gene Therapy", Jul. 1999, pp. 1619-1632, vol. 10, No. 10, (Abstract Only Provided).
Kratz, Peter A., et al., "Native display of complete foreign protein domains on the surface of hepatitis B virus capsids ", "Proc. Natl. Acad. Sci. USA", Mar. 2, 1999, pp. 1915-1920, vol. 96, No. 5.
Moffatt, S., et al., "A cytotoxic nonstructural protein, NS1, of human parvovirus B19 induces activation of interleukin-6 gene expression ", "J. Virol.", Dec. 1996, pp. 8485-8491, vol. 70, No. 12.
Musiani, Monica, et al., "Immunoreactivity against linear epitopes of parvovirus B19 structural proteins. Immunodominance of the amino-terminal . . . ", "Journal of Medical Virology", 2000, pp. 347-352, vol. 60.
Ozawa, K. et al., "Characterization of Capsid and Noncapsid Proteins of B19 Parvovirus Propagated in Human Erythroid Bone Marrow Cell . . . ", "Journal of Virology", Aug. 1897, pp. 2627-2630, vol. 61, No. 8.
Stripecke, R., et al., "Immune response to green fluorescent protein: implications for gene therapy", "Gene Therapy", 1999, pp. 1305-1312, vol. 6, Publisher: Stockton Press.
Takahashi, Naoko, et al., "Genetic heterogeneity of the immunogenic viral capsid protein region of human parvovirus B19 isolates obtained from . . . ", "FEBS Letters", 1999, pp. 289-293, vol. 450.
Zadori, Zoltan, et al., "A Viral Phospholipase A2 Is Required for Parvovirus Infectivity", "Developmental Cell", Aug. 2001, pp. 291-302, vol. 1, No. 2.

* cited by examiner

*Primary Examiner* — Mary E Mosher
(74) *Attorney, Agent, or Firm* — Hultquist, PLLC; Steven J. Hultquist; Kelly K. Reynolds (57) ABSTRACT

The present invention provides a composition comprising (a) a parvovirus NS1 protein and (b) a parvovirus VP1 protein. Furthermore, the present invention provides DNA sequences encoding said proteins. The composition of the invention is useful for the preparation of a toxin for treating tumoral diseases.

7 Claims, 7 Drawing Sheets

SEQUENCE LISTING

<160> NUMBER OF SEQ ID NOS: 13

<210> SEQ ID NO 1
<211> LENGTH: 30
<212> TYPE: DNA
<213> ORGANISM: Artificial Sequence
<220> FEATURE:
<223> OTHER INFORMATION: Synthetic Construct

<400> SEQUENCE: 1
atgactccat ggcgcctcca gctaaaaaga        30

<210> SEQ ID NO 2
<211> LENGTH: 35
<212> TYPE: DNA
<213> ORGANISM: Artificial Sequence
<220> FEATURE:
<223> OTHER INFORMATION: Synthetic Construct

<400> SEQUENCE: 2
tcgcccttgc tcaccatcgt ttgactcctt tgctg        35

<210> SEQ ID NO 3
<211> LENGTH: 33
<212> TYPE: DNA
<213> ORGANISM: Artificial Sequence
<220> FEATURE:
<223> OTHER INFORMATION: Synthetic Construct

<400> SEQUENCE: 3
aggagtcaaa cgatggtgag caagggcgag gag        33

<210> SEQ ID NO 4
<211> LENGTH: 32
<212> TYPE: DNA
<213> ORGANISM: Artificial Sequence
<220> FEATURE:
<223> OTHER INFORMATION: Synthetic Construct

<400> SEQUENCE: 4
acggtctcga gtagcgaccg gcgctcagtt gg        32

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
ggtcaatcta ttcgcattga t        21

<210> SEQ ID NO 6
<211> LENGTH: 30
<212> TYPE: DNA
<213> ORGANISM: Artificial Sequence
<220> FEATURE:
<223> OTHER INFORMATION: Synthetic Construct

```
<400> SEQUENCE: 6
gaggcgccat gtccaagttc agcggctcgc                                    30

<210> SEQ ID NO 7
<211> LENGTH: 30
<212> TYPE: DNA
<213> ORGANISM: Artificial Sequence
<220> FEATURE:
<223> OTHER INFORMATION: Synthetic Construct

<400> SEQUENCE: 7
gaacttggac atggcgcctc cagctaaaag                                    30

<210> SEQ ID NO 8
<211> LENGTH: 33
<212> TYPE: DNA
<213> ORGANISM: Artificial Sequence
<220> FEATURE:
<223> OTHER INFORMATION: Synthetic Construct

<400> SEQUENCE: 8
atacgcccgg gctaggtttg actgctttgc tgt                                33

<210> SEQ ID NO 9
<211> LENGTH: 34
<212> TYPE: DNA
<213> ORGANISM: Artificial Sequence
<220> FEATURE:
<223> OTHER INFORMATION: Synthetic Construct

<400> SEQUENCE: 9
atacgagatc tgtttaaacc aaggcgcgaa aagg                               34

<210> SEQ ID NO 10
<211> LENGTH: 7
<212> TYPE: PRT
<213> ORGANISM: Parvovirus
<220> FEATURE:
<221> NAME/KEY: SOURCE
<222> LOCATION: (1)..(7)
<223> OTHER INFORMATION: PLA2 motif in VP1

<400> SEQUENCE: 10

Tyr Pro Gly Asn Ser Leu Asp
1               5

<210> SEQ ID NO 11
<211> LENGTH: 11
<212> TYPE: PRT
<213> ORGANISM: Parvovirus
<220> FEATURE:
<221> NAME/KEY: SOURCE
<222> LOCATION: (1)..(11)
<223> OTHER INFORMATION: PLA2 motif in VP1

<400> SEQUENCE: 11

Asp Ala Ala Ala Lys Glu His Asp Phe Arg Tyr
1               5                   10

<210> SEQ ID NO 12
<211> LENGTH: 10
<212> TYPE: PRT
<213> ORGANISM: Parvovirus
<220> FEATURE:
<221> NAME/KEY: SOURCE
<222> LOCATION: (1)..(10)
<223> OTHER INFORMATION: PLA2 motif in VP1
```

```
-continued

<400> SEQUENCE: 12

Ser Ala Ala Asp Glu Lys Phe Ile Lys Glu
1               5                   10

<210> SEQ ID NO 13
<211> LENGTH: 7
<212> TYPE: PRT
<213> ORGANISM: Parvovirus
<220> FEATURE:
<221> NAME/KEY: SOURCE
<222> LOCATION: (1)..(7)
<223> OTHER INFORMATION: PLA2 motif in VP1

<400> SEQUENCE: 13

Tyr Phe Arg Ala Lys Arg Ala
1               5
```

COMPOSITIONS COMPRISING A PARVOVIRUS VP1-VARIANT AND A PARVOVIRUS NS1 PROTEIN FOR INDUCTION OF CYTOLYSIS

CROSS-REFERENCE TO RELATED APPLICATIONS

This application is a divisional of U.S. patent application Ser. No. 10/483,234 filed on Jan. 8, 2004 and published on Oct. 21, 2004 as U.S. patent application Publication No. 2004/0208886 A1, which in turn claims priority under 35 U.S.C. §371 of International Application No. PCT/EP02/07706, filed Jul. 10, 2002 and published on Jan. 23, 2003 as International Patent Application Publication No. WO 2003/006067, which further claims priority of European Patent Application No. 01116856.4, filed Jul. 10, 2001. The disclosures of all such U.S., international and European patent applications are hereby incorporated herein by reference in their respective entireties, for all purposes.

FIELD OF THE INVENTION

The present invention relates to a composition comprising (a) a parvovirus NS1 protein and (b) a parvovirus VP1 protein. Furthermore, the present invention relates to DNA sequences encoding said proteins. The composition of the invention is useful for the preparation of a toxin for treating tumoral diseases.

BACKGROUND OF THE INVENTION

Parvovirus designates a genus of the virus family Parvoviridae. The parvovirus genus comprises a number of small, icosaedric viruses that can replicate in the absence of a helper virus. Parvovirus contains a single-stranded DNA having a length of about 5.000 bp. At the 3' and 5' ends of the DNA there is one palindromic sequence each. The DNA codes for two capsid proteins, VP1 and VP2, as well as for two regulatory non-structure proteins, NS1 and NS2. The latter proteins are phosphorylated and show nuclear or both cytoplasmic and nuclear localization, respectively. The two capsid proteins VP1 and VP2 are encoded by overlapping open reading frames so that the VP2 encoding region is entirely comprised within the VP1 encoding region. In a natural infection capsid proteins are expressed in a VP1:VP2 ratio of 1:10 due to alternative splicing. Recently it has been shown that the region of the capsid proteins which is specific for VP1 (N-terminal region) contains motifs common to cellular phospholipase A and indeed exerts this activity in vitro. The calcium dependent, secreted $PLA_2$ to which parvovirus VP1 shares similarities, takes part in signaling pathways that involve cell lysis by permeabilizing membranes. On the other hand, NS1 has been shown to be regulated by members of the protein kinase C family, which in turn are subject to regulation through phospholipases.

Parvoviruses are usually well-tolerated by populations of their natural host, in which they persist without apparent pathological signs. This is due to both the protection of foetuses and neonates by maternal immunity, and the striking restriction of parvovirus replication to a narrow range of target proliferating tissues in adult animals. This host tolerance concerns especially rodent parvoviruses, for example the minute virus of mice (MVM) and H-1 virus in their respective natural hosts, namely mice and rats. In addition, humans can be infected with the latter viruses, without any evidence of associated deleterious effects from existing epidemiological studies and clinical trials. On the other hand, autonomous parvoviruses have been shown to preferentially propagate in and to kill neoplastically transformed cells. In addition, they consist of a class of viruses that, despite causing viremia in their infected hosts, mostly produce an apathogenic infection. For these reasons, autonomous parvoviruses are thought to be excellent tools for cancer gene therapy. Particular interests are focused on recombinant vectors maintaining their natural oncotropism, as well as their oncolytic and oncosuppressive potential.

NS1, the major non-structural protein is necessary for viral DNA replication and participates in the regulation of viral gene expression. Particularly, NS1 transactivates the promoter P38 and exhibits DNA-binding, helicase and DNA-nicking activities. Furthermore, NS1 induces cytotoxic and/or cytostatic stress in sensitive host cells.

Therefore, it seems advisable to keep NS1 within parvoviral vectors, in order to (a) maintain their specific competence for NS1-dependent DNA replication and gene expression in tumour cells, resulting in an enhanced production of therapeutics agents at the desired locus (oncotropism), (b) take advantage of NS1 cytotoxicity to kill neoplastic cells and shed tumour antigens to elicit anti-cancer immunity (oncolysis), and (c) achieve still unknown effects that may contribute to the persistence (memory) of a tumour-free status (oncosuppression).

Current parvoviral vectors harbor the wild type genes (for the above discussed reasons) and either of a variety of different transgenes aimed to induce anti-tumoral responses. In most applications considered to date, the transgenes were chosen for their capacity to upmodulate the host cellular immunity against cancer. While the transgene expression induced by such vectors was successfully targeted at the location of the tumour and was especially high, duration of the therapy was relatively short, i.e. three to five days, which is likely due to the NS1-induced killing of transduced cells. New developments concerning the regulation of the NS1 protein have shown that the cytotoxicity of this protein is a regulated process. Furthermore, NS1 variants have been produced by site-directed mutagenesis of putative regulatory elements, which are up- and down-modulated regarding their cytotoxic potential while keeping replicative functions (European patent application No. 99115161.4). These variants may allow a prolongated expression of transgenes harbored by parvoviral vectors (less toxic variants) or endow infectious parvoviruses with an enhanced oncotoxicity (more toxic variants).

Considering the use of NS1 as an oncotoxin in the context of parvoviral, but also non-parvoviral vectors it should be stated that, though able to induce apoptosis in certain cancer cells (leukemias), NS1 alone often causes only a cytostatic effect that is accompanied by morphological changes (cell shrinking) and a dramatic disorganisation of the cytoskeleton in the absence of cell lysis or apoptotic signs. NS1-expressing cells remain on a long-term in this state that has, thus, common features with a terminal differentiation. This NS1-mediated induction of a cellular terminal state is interesting on its own right for limiting tumour cell proliferation, yet it is not suitable to trigger the uptake of tumour-associated antigens (TAAs) by presenting cells of the immune system, which requires tumour cell death. This is a very serious limitation of the use of NS1 alone: Given that only a minor fraction of tumour cells can be expected to be killed, it is crucial that the direct toxicity of the vector (affecting only transduced cells)

is enhanced by the immune system in order to achieve a bystander suppressive effect on non-infected tumour cells.

SUMMARY OF THE INVENTION

Therefore, it is the object of the present invention to provide a means for improving the therapeutic usefulness of NS1, e.g. as regards the NS1 cytotoxicity to kill neoplastic cells and shed tumour antigens to elicit anti-cancer immunity.

According to the invention this is achieved by the subject matters defined in the claims.

Figure 1A:
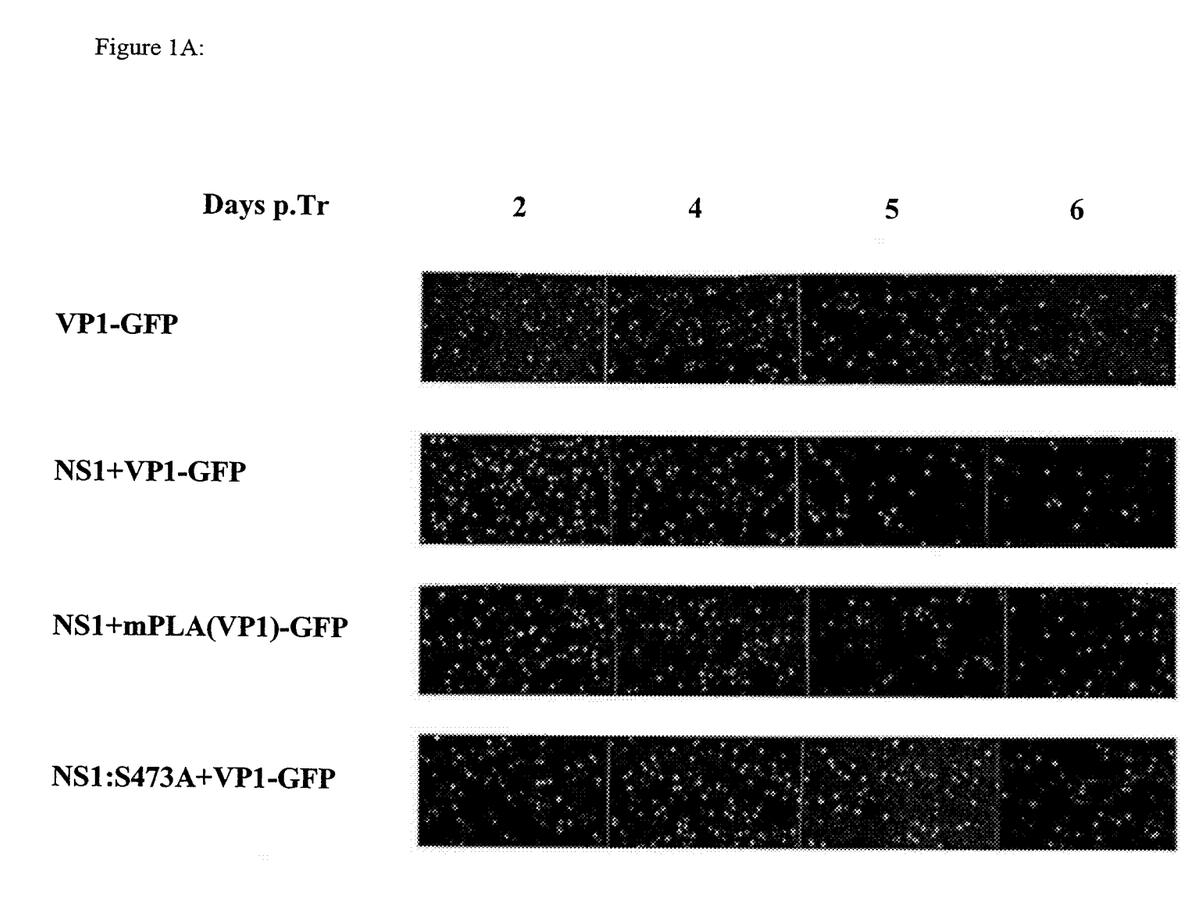
Figure 1B:
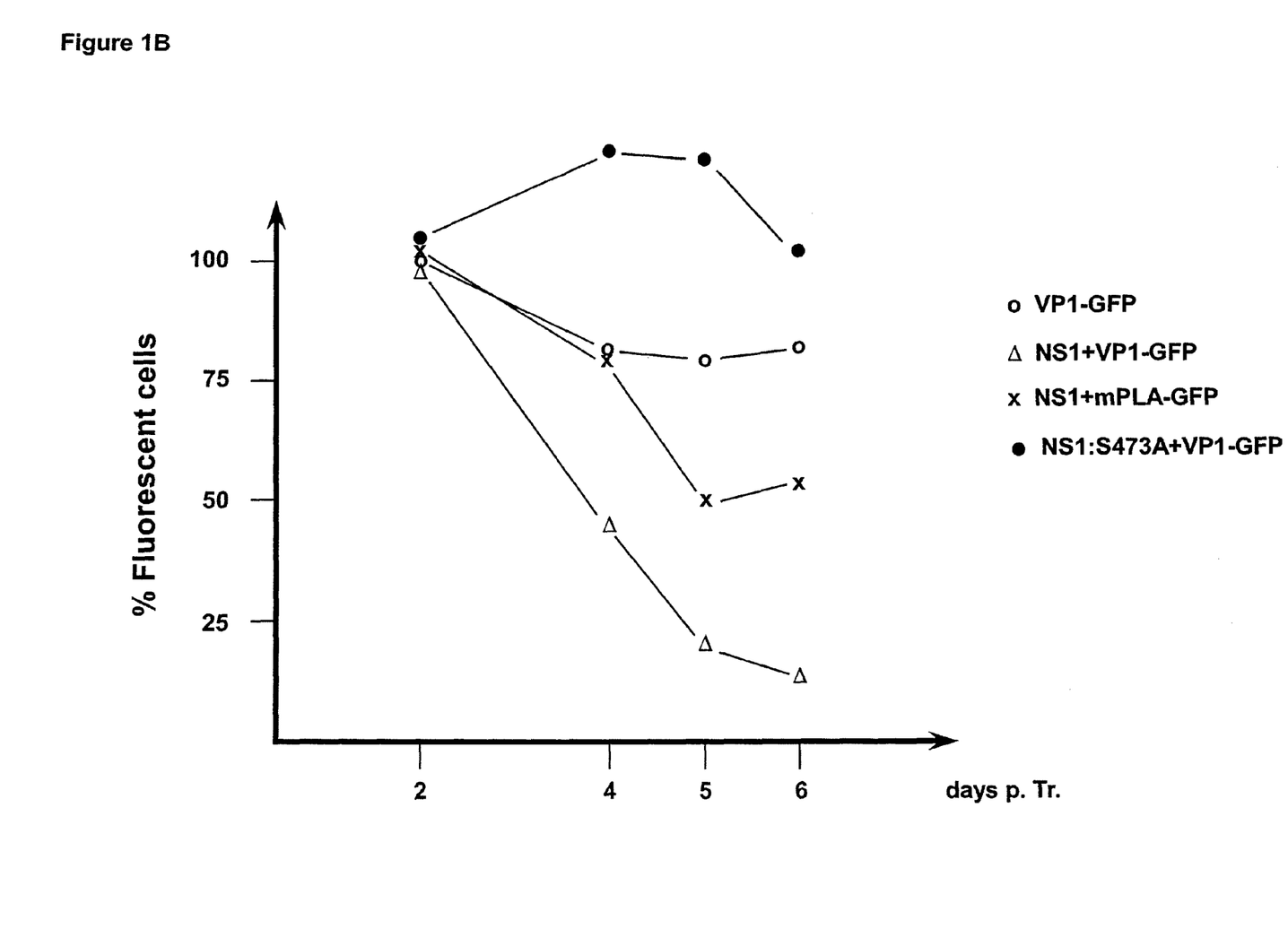
Figure 1C:
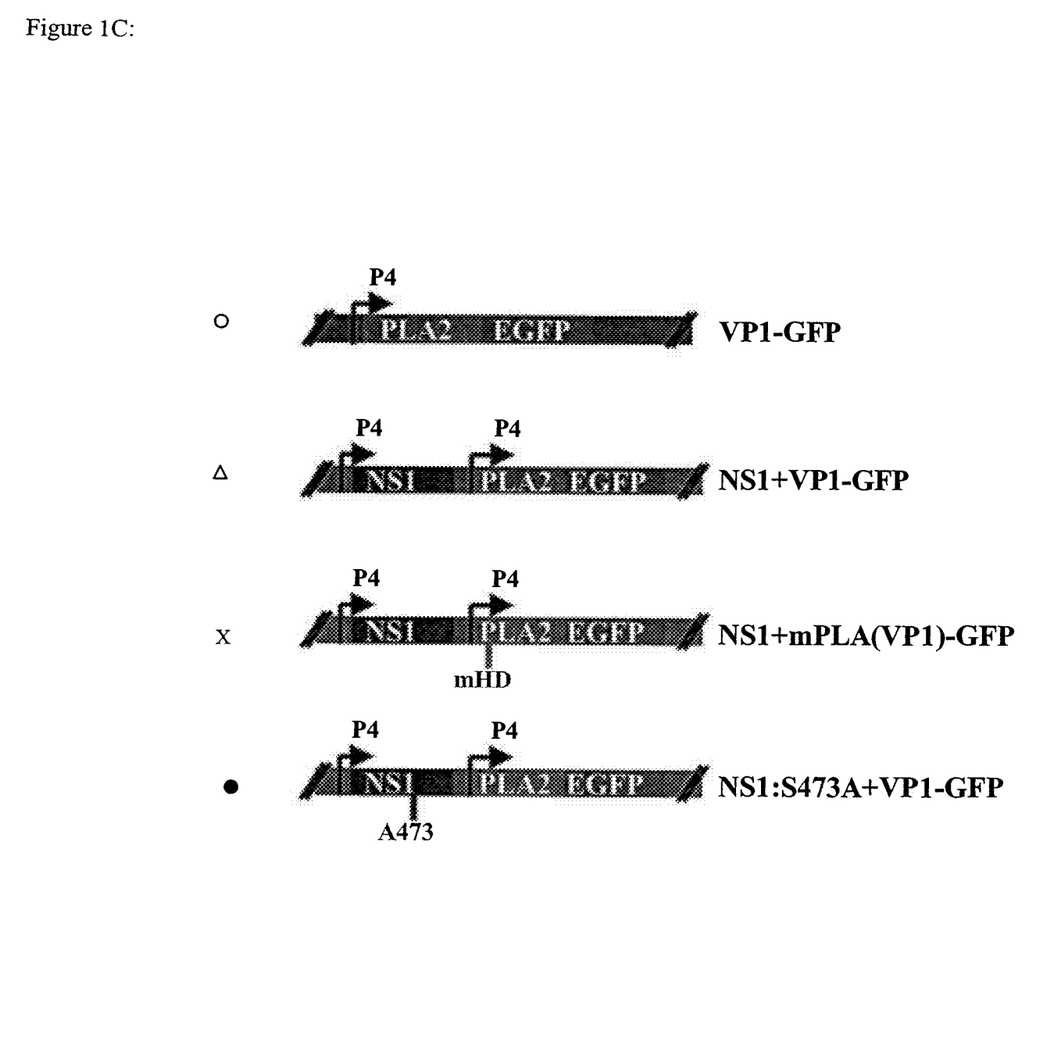
Figure 4:
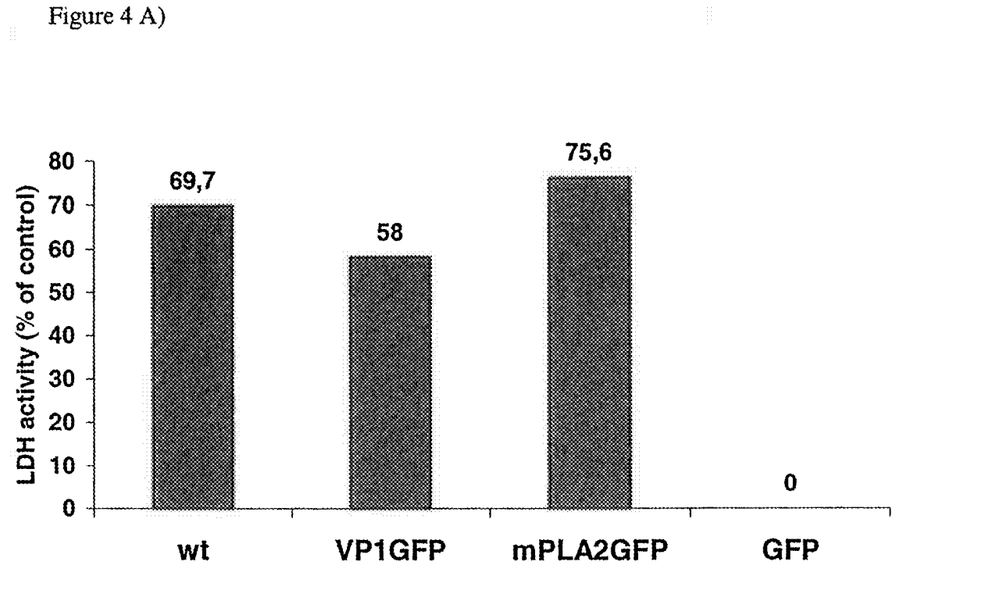
Figure 4B:
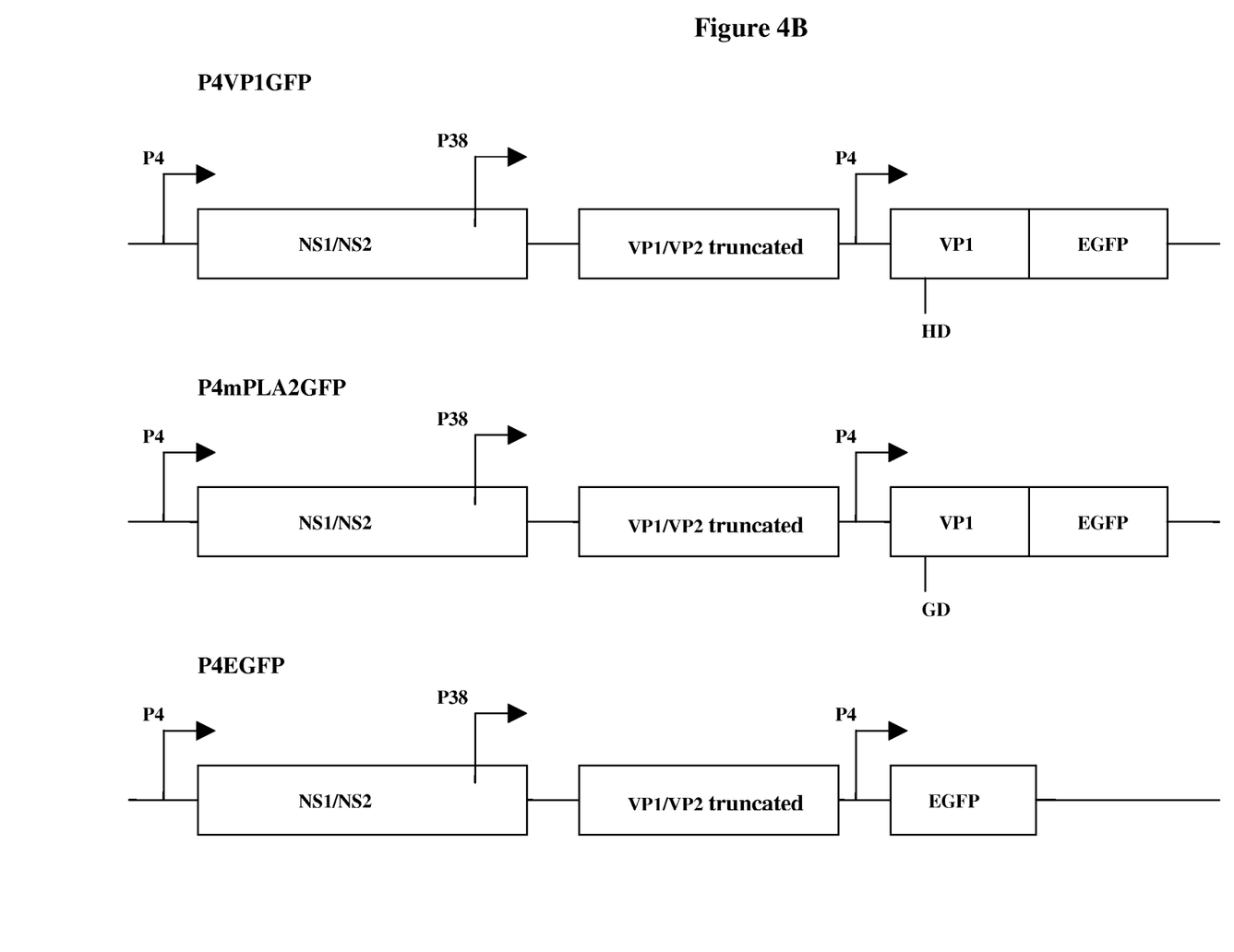

The present invention is based on the applicant's finding of a new toxin which is a combination of two parvoviral products, the NS1 protein and the capsid VP1 protein or a part thereof. Since VP1 is a large protein (83 kDa, 2453 bp ORF) which is itself subject to regulation (it is post translationally modified), small fusion proteins were constructed containing a VP1-specific region and expressed together with the effector protein NS1 upon transfection in mammalian cells. While being well tolerated by the cells on their own, the fusion proteins significantly increased the intrinsic cytotoxicity of NS1 as measured by the disappearance of VP1/NS1 containing cells in a function of time (monitored by fluorescent proteins present in transfected cells; see FIG. 1). This increased toxicity is manifested in an region and expressed together with the effector protein NS1 upon transfection in mammalian cells. While being well tolerated by the cells on their own, the fusion proteins significantly increased the intrinsic cytotoxicity of NS1 as measured by the disappearance of VP1/NS1 containing cells in a function of time (monitored by fluorescent proteins present in transfected cells; see FIG. 1). This increased toxicity is manifested in an induction of cytolysis as apparent by the release of lactate dehydrogenase (LDH) in the presence of both wild type NS1 and the VP1 specific region, a feature that is absent upon the sole expression of wild type NS1 (FIG. 4). In this regard it has to be stated that the toxic effects of NS1 and VP1 could be mutual in a way that not only VP1 is increasing NS1 toxicity, but also that NS1 is able to activate VP1 induced cytolysis. To conclude, this new toxin is endowed with an enhanced capacity for causing cell death and not merely cell proliferation arrest. In the cellular system analysed, the NS1-VP1 toxin proved to have an enhanced lytic activity. Thus, tumorally expressed NS1-VP1 toxin is endowed with an enhanced capacity to kill tumour cells, which in its turn should stimulate the loading of presenting cells with TAAs and the activation of an anticancer immune response.

According to the present invention, the applicant's findings are used to provide a composition comprising (a) a parvovirus NS1 protein and (b) a parvovirus VP1 protein.

The expression "parvovirus" comprises any parvovirus, particularly a rodent parvovirus, such as minute virus of mice (MVM) and H-1 virus.

The expression "NS1 protein" comprises any NS1 protein, i.e. the native protein obtainable form the parvoviruses described above as well as modified versions thereof which are biologically active (see, e.g., Genebank Accession No: P03134; Astell et al., Nucleic Acids Res. 11 (1983), 999-1018). Such modified versions of the NS1 protein also comprise the mutants disclosed in the European patent application No. 99115161.4.

The expression "VP1 protein" comprises any VP1 protein, i.e. the native protein obtainable from the parvoviruses described above as well as modified versions and fusion proteins which are still biologically active (see, e.g., Genebank Accession No: P03137; Astell et al., Nucleic Acids Res. 11 (1983), 999-1018). Examples of modified versions are truncated and mutant forms of the VP1 protein.

The expression "comprising a parvovirus NS1 protein and a parvovirus VP1 protein" also comprises NS1-VP1 fusion proteins. NS1-VP1 fusion proteins comprise any NS1-VP1 fusion protein which exhibits the biological activity of both protein partners. Preferably, the NS1 protein corresponds to the N-terminal partner of the fusion protein. DNA sequences encoding such proteins can be designed by the person skilled in the art by well known methods. The person skilled in the art is also in a position to design DNA sequences encoding a fusion protein, wherein the NS1- and VP1-protein, respectively, is (are) truncated but still active.

Assays for monitoring the biological activities of the proteins (VP1; $PLA_2$-activity) are well known to the person skilled in the art and can be carried like measurements of arachidonic acid release (Balsinde et al., PNAS USA 95 (1998), 7951-7956) or production of prostaglandin E2 (Newton et al., 1998, IBC 48, 32312-21) or as described in Example 2, below.

In a preferred embodiment, the VP1 protein is fused to a carrier protein allowing, e.g., to detect the expression of the VP1 protein in a host cell. Particularly preferred are the carrier proteins green fluorescent protein (GFP), NS1, IL-2, IP10, Cytatines, Cro, or signaling peptides targeting the protein to distinct locations within the cell.

In a more preferred embodiment, the VP1 protein (or the VP1 partner of the fusion protein) is a truncated protein which still exhibits the desired biological activity. Such truncated versions of the VP1 protein can be generated by the person skilled in the art according to standard methods. The biological activity of the VP1 fragments can be assayed, e.g. by the method described in Example 2, below.

In an even more preferred embodiment, the truncated VP1 protein comprises the VP1 domain exhibiting phospholipase A activity. This activity is localised within the specific N-terminal part of the VP1 protein (residues 1 to 142) (see FIG. 2; Zadori et al. (2000), VIIIth Parvovirus Workshop Mont Tremblant, Quebec, Canada.)

A further subject matter of the present invention relates to (a) DNA sequence(s) encoding the proteins of the composition of the invention described above. A DNA sequence according to the present invention can be present in a vector and expression vector, respectively. A person skilled in the art is familiar with examples thereof. In the case of an expression vector for *E. coli* these are e.g. pGEMEX, pUC derivatives, pGEX-2T, pET3b, T7 based expression vectors and pQE-8. For the expression in yeast, e.g. pY1OO and Ycpad1 have to be mentioned while e.g. pKCR, pEFBOS, cDM8, pMSCND, and pCEV4 have to be indicated for the expression in animal cells. The baculovirus expression vector pAcSGHis NT-A is especially suitable for the expression in insect cells.

In a preferred embodiment, the vector containing the DNA sequence(s) according to the invention is a virus, e.g. anadenovirus, vaccinia virus, an AAV virus or a parvovirus, such as MVM or H-1, a parvovirus being preferred. The vector may also be a retrovirus, such as MoMULV, MoMuLV, HaMuSV, MuMTV, RSV or GaLV. Suitable promoters include the strong constitutive human or mouse cytomegalovirus (CMV) immediate early promoter, the inducible P38 parvovirus promoter, the parvovirus P4 promoter and tissue and tumour specific promoters.

For constructing expression vectors which contain the DNA sequence(s) according to the invention, it is possible to use general methods known in the art. These methods include e.g. in vitro recombination techniques, synthetic methods and in vivo recombination methods as described in Sambrook et al., supra, for example.

Furthermore, the present invention relates to host cells which contain the above described vectors. These host cells include bacteria, yeast, insect and animal cells, preferably mammalian cells. The E. coli strains HB101, DH1, x1776, JM101, JM109, BL21, XL1Blue and SG 13009, the yeast strain Saccharomyces cerevisiae and the animal cells L, A9, 3T3, FM3A, CHO, COS, Vero, HeLa and the insect cells sf9 are preferred. Methods of transforming these host cells, of phenotypically selecting transformants and of expressing the DNA according to the invention by using the above described vectors are known in the art.

The present invention also relates to a method of producing the composition of the invention comprising the culturing of the transformant described above under suitable conditions and isolating the protein(s) of the composition from the transformant or the medium. Methods for culturing said transformants, isolating and purifying the protein(s) are well known to the person skilled in the art.

Moreover, the present invention relates to a pharmaceutical composition comprising the above described compounds. For administration these compounds are preferably combined with suitable pharmaceutical carriers. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Administration of the composition may be effected by different ways, e.g. by intravenous, intraperetoneal, subcutaneous, intramuscular, topical or intradermal administration. The route of administration, of course, depends on the nature of the disease, e.g. tumour, and the kind of compound(s) contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind of the tumour, general health and other drugs being administered concurrently.

The composition of the present invention can be administered in the form of proteins (protein injection or protein delivery into the desired tumour cells) or (a) genetic element(s) encoding said proteins, supplied as free molecules or through a viral, e.g. parvoviral, or non-viral vector. Suitable vectors and methods for in vitro- or in vivo-gene therapy are described in the literature and are known to the persons skilled in the art; see, e.g., WO 94/29469 or WO 97/00957. The DNA sequences encoding the proteins of the composition of the present invention can be administered directly to the target site, e.g., by ballistic delivery, as a colloidal dispersion system or by catheter to a site in artery. The colloidal dispersion systems which can be used for delivery of the above DNA sequences include macromolecule complexes, nanocapsules, microspheres, beads and lipid-based systems including oil-in-water emulsions, (mixed) micelles, liposomes and lipoplexes. The preferred colloidal system is a liposome. The composition of the liposome is usually a combination of phospholipids and steroids, especially cholesterol. The skilled person is in a position to select such liposomes which are suitable for the delivery of the desired DNA molecule. Organ-specific or cell-specific liposomes can be used, e.g. in order to achieve delivery only to the desired tissue. The targeting of liposomes can be carried out by the person skilled in the art by applying commonly known methods. This targeting includes passive targeting (utilizing the natural tendency of the liposomes to distribute to cells of the RES in organs which contain sinusoidal capillaries) or active targeting (for example by coupling the liposome to a specific ligand, e.g., an antibody, a receptor, sugar, glycolipid, protein etc., by well known methods). In the present invention monoclonal antibodies are preferably used to target liposomes to specific tumours via specific cell-surface ligands.

The treatment can be given to cell cultures or organisms, e.g. tumour bearing organisms. Should both proteins of the present invention be administered as separated genetic elements, time intervals between their respective administration can be applied. Alternatively, stably transfected cell lines expressing the VP1 protein can be produced. In the absence of NS1, the VP1 component is well tolerated by host cells over extended periods of time. The cytolytic effect is exerted only when the VP1 component is coexpressed with the NS1 component. It is, thus, possible to select tumour cell lines that stably express the VP1 component and contain (or not) an inducible clone of the NS1 component that is kept silent. Upon NS1 expression (as a result of NS1 gene transfer or induction) the tumour cells get lyzed, which can be achieved in vitro or in vivo (after transplantation of VP1 expressing cells) in order to trigger the release, uptake and presentation of tumour-associated antigens. Moreover, the composition of the invention or the corresponding DNA sequences can be applied in combination with other agents (such as cytokines) in gene and cancer therapy approaches.

Finally, the present invention relates to the use of the above described compounds (protein composition, DNA sequences or expression vectors) for the preparation of a toxin for treating tumoral diseases.

BRIEF DESCRIPTION OF THE DRAWINGS

FIG. 1: A9 cells grown on Spot-Slides (NeoLab, Heidelberer, Deutschland) were transfected with the indicated constructs (100 ng/well) using 1 μL Lipofectamine (GibcoBRL, Karlsruhe, Deutschland). Transfected, living cells were identified by their green fluorescence and monitored in daily intervals using a reverse angle fluorescence Microscope (Leica IL2).

(A) Photographs of fluorescent, transfected cells obtained after 2, 4, 5 and 6 days post transfection.

(B) Statistical evaluation of NS1/VP1 toxicity. Transfected, GFP expressing (fluorescent) cells were counted at daily intervals and their survival was expressed as percentage of the number of fluorescent cells at day 2 post transfection.

(C) Schematic presentation of the effector constructs expressing $PLA_2$ (the active domain of the VP1 polypeptide) and/or NS1 parvovirus MVM. Both effect or genes are expressed under the control of the parvoviral P4 promoter. To monitor cells containing transfected DNA, the gene for the green fluorescent protein was fused to the $PLA_2$ domain. The phosphorylation site mutant NS1:S473A (Dettwiler et al., J. Virol. 73 (1999), 7410-7420) was chosen as a representative non-toxic NS1 mutant. Mutant $PLA_2$ was generated by PCR replacing the HD-motif (aa 41/42), i.e. the active site of the $PLA_2$ enzyme, by methionine residues. Toxicity assay was carried out according to Corbau et al., Virology 278 (2000), 151-167.

As shown in (A) and (B), wild type NS1 and the $PLA_2$-domain of VP1 acted synergistically in that this cytotoxicity of coexpressed active polypeptides was in comparison with the effect of each effector protein alone, as revealed by the disappearance of fluorescent/transfected cells.

FIG. 2: Schematic representation of the parvovirus VP proteins VP1, the large 83 kDa capsid protein comprises 716 amino acids while VP2 lacks the 142 N-terminal amino acids and starts at methionine 143 due to alternative splicing of the precursor mRNAs. The VP1 unique region is represented as a hatched box.

Figure 2:
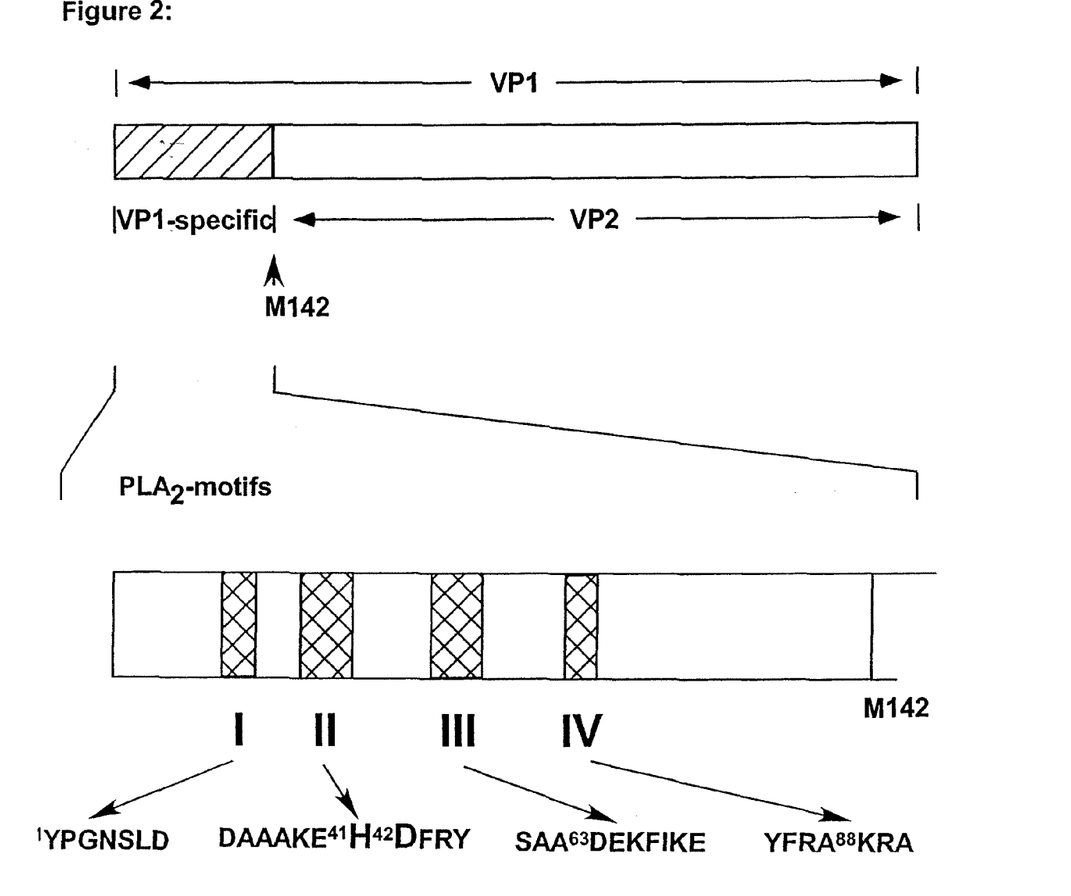

Blow-up of the VP1-specific region comprising amino acids 1 to 142 of the VP1 protein. The four motifs (SEQ ID NOs: 10-13) showing homology to cellular $PLA_2$s are indicated as crossed regions and the corresponding amino acid sequences of VP1 are given on the bottom. The putative active site for PLA2-activity is indicated by capitals.

Figure 3A:
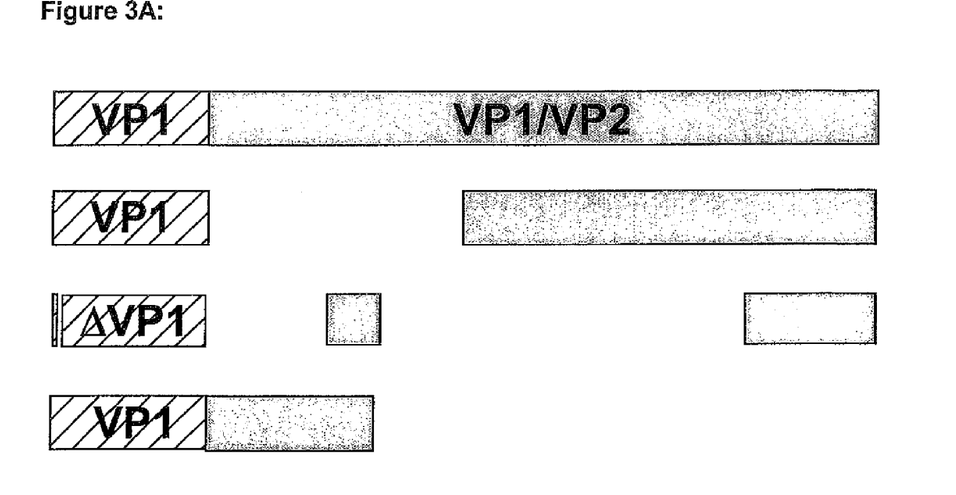
Figure 3B:
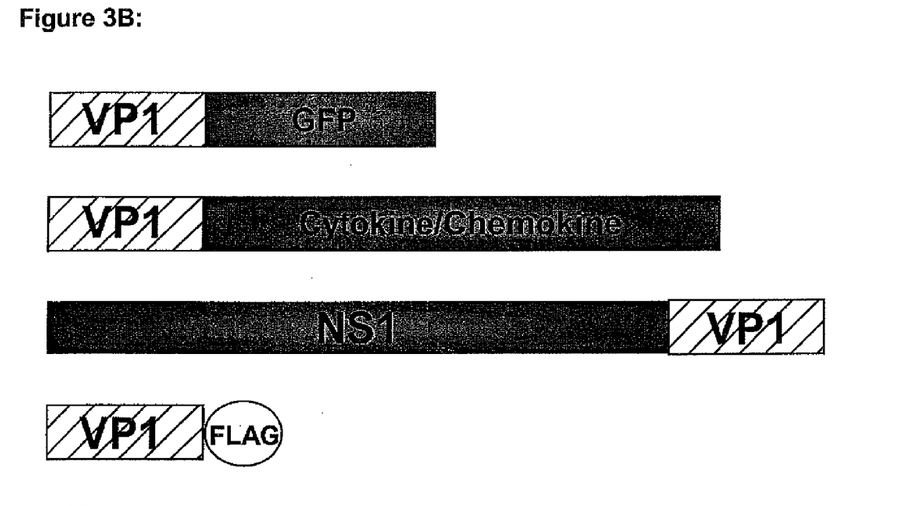
Figure 3C:
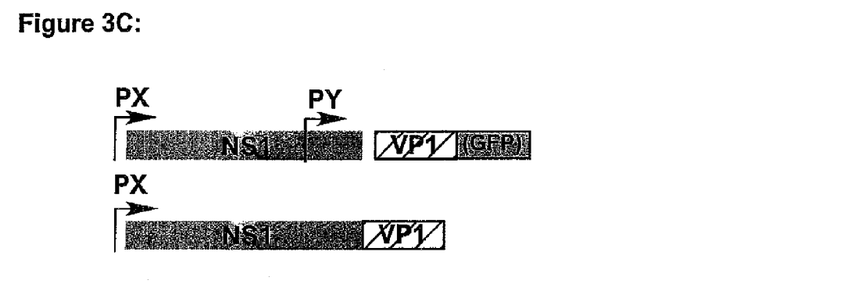

FIG. 3: Schematic representation of examples of VP1 and VP1 variants designed for use of the present invention
(A) VP1 deletion mutants of various sizes
(B) VP1 fusion peptides using "carrier"-polypeptides; and
(C) Examples of cassettes for the expression of VP1-variants to obtain synergistic effects together with NS1.

FIG. 4
(A) The experiment involves the use of the Promega kit "CytoTox 96®" non-radioactive cytotoxicity assay (Promega, Mannheim, Deutschland). LDH is a cytosolic enzyme that is released upon cell lysis. Released LDH is measured using an enzymatic assay which results in the conversion of a tetrazolium salt (INT) into a red formazan product. The color intensity, measured with a standard 96 well plate reader at 490 nm, is proportional to the number of lysed cells. Experiments were performed in 96 well plates containing 2000 mouse A9 cells per well. Infection was carried out 24 hours after spreading of the cells at a multiplicity of 10 infectious units of virus per cell. Culture medium was collected 6 days after transfection and directly tested for LDH activity as described by the manufacturer. The total amount of LDH in the cells stands for 100%

(B) Schematic representation of VP1 constructs used for the LDH assay. Their construction is detailed in Example IC.

The present invention is explained by the examples.

EXAMPLE 1

Construction of Vectors for Expression of VP1 Variants

(a) pP4-VP1-GFP

The coding sequence for the VP1-GFP fusion protein was obtained by chimeric polymerase chain reaction (PCR) using the primer pair 5'-ATG ACT CCA TGG CGC CTC CAG CTA AAA AGA-3' (A) (SEQ ID NO: 1) and 5'-TCG CCC TTG CTC ACC ATC GTT TGA CTC CTT TGC TG-3' (B) (SEQ ID NO: 2) using as template pTM1-VP1 to obtain the coding sequence for the VP1-specific domain of parvovirus VP-proteins. The primer pair 5'-AGG AGT CAA ACG ATG GTG AGC AAG GGC GAG GAG-3' (C) (SEQ ID NO: 3) and 5'-ACG GTC TCG AGT AGC GAC CGG CGC TCA GTT GG-3' (D) (SEQ ID NO: 4) with pEGFP (Clontech, Heidelberg, Deutschland) as a template was used to obtain the GFP encoding sequence. In a second PCR reaction the VP1- and GFP-fragments were annealed due to overlapping sequences and further amplified using primers A and D. After amplification the PCR product was digested with the restriction endonucleases NcoI and XbaI and ligated into the similarly cleaved vector pDB-MVMp; see FIG. 1C. pDB-MVMp constitutes an infectious molecular clone of MVMp (Kestler et al., Hum. Gene Ther. 10 (1999), 1619-1632).

(b) pP4-NS1-VP1

The construct constitutes an eukaryotic expression vector under the control of the parvovirus P4 promoter (S-phase/transformation regulated). The coding sequence for the NS1-VP1 fusion protein was obtained by chimeric PCR using the primer pair 5'-GGT CAA TCT ATT CGC ATT GAT-3' (A) (SEQ ID NO: 5) and 5'-GAG GCG CCA TGT CCA AGT TCA GCG GCT CGC-3' (B) (SEQ ID NO: 6) for amplification of the template pTM1-NS1 Nuesch et al., Virology 191 (1992), 406-416) to obtain the full-length NS1 fragment. The primer pair 5'-GAA CTT GGA CAT GGC GCC TCC AGC TAA AAG-3' (C) (SEQ ID NO: 7) and 5'-ATA CGC CCG GGC TAG GTT TGA CTG CTT TGC TGT-3' (D) (SEQ ID NO: 8) with pTM1-VP1 as a template was used for obtaining the VP1 coding sequence. In a second round of PCR the two fragments were combined using primers A and D. After amplification the PCR product was digested with the restriction endonucleases XhoI and SmaI and ligated into XhoI and StuI digested vector pTHis-NS1 (Nüesch et al., Virology 209 (1995), 122-135). To obtain pP4-NS1-VP1, the coding sequence of the NS1-VP1 variant was amplified by PCR using an N-terminal primer containing a SmaI restriction site together with a C-terminal primer containing an XbaI cleavage site. This SmaI to XbaI NS1-VP1 fragment wad then transferred into EcoRV and XbaI cleaved pP4-GFP. Clone pP4-NS1-VP1 was deposited on May 15, 2001, with the DSMZ under accession number DSM 14300 according to the regulations of the Budapest treaty.

(c) pP4-NS1+2-P4-VP1-GFP

To obtain pP4-NS1-P4-VP1-GFP used for transfection experiments, the PmeI to XbaI fragment of pP4-VP1-GFP (or for controls pP4-GFP, pP4-mPLA-GFP) was transferred into the StuI and XbaI cleaved pDB-MVMp or pDB-NS1:S473A (Corbau et al., Virology 278 (2000), 151-167).

To obtain pP4-NS1+2-P4-VP1-GFP recombinant MVM virus; the P4-VP1-GFP fragment was amplified using a primer 5'-ATA CGA GAT CTGTTT AAA CCA AGG CGC GAA AAG G-3' (SEQ ID NO: 9) within the P4 promoter region containing an N-terminal BglII cleavage site and primer D within the C-terminus of GFP harbouring an XbaI site. This BglII to XbaI fragment was then cloned into the BglII and XbaI cleaved capsid region of pDB-MVMp. Clone pP4-NS1+Z-P4-VP1-GFP was deposited on May 15, 2001, with the DSMZ under accession number DSM 14301 according to the regulations of the Budapest treaty.

Similarly, the BglII to XbaI fragments of P4-GFP and P4-mPLA-GFP were transferred into the infectious DNA clone of MVMp.

EXAMPLE 2

Toxicity Assays

(a)

A9 cells grown on Spot slides (Neolab) were transfected with the constructs described in Example 1, above, and shown in FIGS. 1C and 3 expressing the GFP (fusion) proteins using lipofectamine. Fluorescent cells were monitored in daily intervals for their overall structure. From the results shown in FIG. 1B it can be concluded that NS1 and VP1 fusion proteins act synergistically to kill the transfected A9 cells. Experimental details are given in the legend of FIG. 1.

(b)

A9 cells were transduced with various multiplicities of recombinant parvoviruses containing VP1-variants or mutants thereof. In daily intervals the release of endogenous LDH (lactate dehydrogenase) was measured using commercial kits in order to obtain measurements for cytolysis. Experimental details are given in the legend of FIG. 4.

What is claimed is:

1. A polynucleotide sequence comprising (a) a DNA sequence encoding a parvovirus NS1 protein and a DNA sequence encoding a fusion protein of a parvovirus VP1 protein and a carrier protein or (b) a DNA sequence encoding a fusion protein of a parvovirus NS1 protein and a parvovirus VP1 protein.

2. The polynucleotide sequence of claim 1, wherein the carrier protein is green fluorescent protein (GFP).

3. The polynucleotide sequence of claim 1, wherein the VP1 protein is a truncated VP1 protein.

4. The polynucleotide sequence of claim 3, wherein the truncated VP1 protein comprises a VP1 domain exhibiting phospholipase A activity.

5. An isolated host cell comprising the polynucleotide of claim 1.

6. An H-1 parvovirus vector comprising the polynucleotide sequence of claim 1.

7. A pharmaceutical composition comprising the polynucleotide sequence of claim 1.

* * * * *